United States Patent
Hammond et al.

(10) Patent No.: US 10,677,727 B2
(45) Date of Patent: Jun. 9, 2020

(54) SCATTERED LIGHT INTEGRATING COLLECTOR

(71) Applicant: University Court of the University of St Andrews, St Andrews (GB)

(72) Inventors: Robert J H Hammond, Fife (GB); Mario E. Giardini, Glasgow (GB); Stephen H. Gillespie, Fife (GB)

(73) Assignee: University Court of the University of St Andrews, St. Andrews (GB)

( * ) Notice: Subject to any disclaimer, the term of this patent is extended or adjusted under 35 U.S.C. 154(b) by 0 days.

(21) Appl. No.: 16/057,594

(22) Filed: Aug. 7, 2018

(65) Prior Publication Data

US 2018/0372631 A1  Dec. 27, 2018

Related U.S. Application Data

(63) Continuation of application No. 15/549,507, filed as application No. PCT/GB2016/050319 on Feb. 10, 2016.

(30) Foreign Application Priority Data

Aug. 8, 2017  (GB) .................................... 15549507

(51) Int. Cl.
G01N 21/51 (2006.01)
G01N 21/47 (2006.01)
(Continued)

(52) U.S. Cl.
CPC ............ *G01N 21/474* (2013.01); *C12Q 1/00* (2013.01); *C12Q 1/02* (2013.01); *C12Q 1/06* (2013.01);
(Continued)

(58) Field of Classification Search
None
See application file for complete search history.

(56) References Cited

U.S. PATENT DOCUMENTS

| | | | |
|---|---|---|---|
| 2,707,900 A | 5/1955 | Maresh et al. | |
| 3,562,524 A | 2/1971 | Moore et al. | |

(Continued)

FOREIGN PATENT DOCUMENTS

| | | |
|---|---|---|
| EP | 2124028 | 11/2009 |
| EP | 2320212 | 5/2011 |

(Continued)

OTHER PUBLICATIONS

Fredborg et al. "Real-Time Optical Antimicrobial Susceptibility Testing," Journal of Clinical Microbiology, Jul. 2013, vol. 51, No. 7, pp. 2047-2053.

(Continued)

*Primary Examiner* — Neil N Turk
(74) *Attorney, Agent, or Firm* — Sheridan Ross P.C.

(57) ABSTRACT

A system for measuring a liquid sample comprising biological material, the system comprising an integrating light collector for collecting light and for at least partially containing the sample; a light source for introducing light in the integrating light collector; a signal generator or modulator configured to cause a known modulation of the light output by the light source; a phase-sensitive detector for detecting scattered light in the integrating light collector; at least one of an exit port to allow un-scattered light to exit the integrating light collector, a beam dump, or a baffle arranged to absorb unscattered light; and a processor configured to analyse the detected modulated light to determine changes in the detected modulated light as a function of time thereby to determine at least one of: drug susceptibility of the biologi- (Continued)

(i)     (ii)

cal material; a change in a number of cells in the sample; a change in cell state; a change in the biological material.

16 Claims, 10 Drawing Sheets

(51) Int. Cl.

| | |
|---|---|
| *C12Q 1/18* | (2006.01) |
| *C12Q 1/02* | (2006.01) |
| *G01N 21/17* | (2006.01) |
| *G01J 3/433* | (2006.01) |
| *G01N 15/06* | (2006.01) |
| *G01J 3/02* | (2006.01) |
| *C12Q 1/00* | (2006.01) |
| *G01N 21/03* | (2006.01) |
| *G01N 21/53* | (2006.01) |
| *G01N 15/02* | (2006.01) |
| *C12Q 1/06* | (2006.01) |
| *G01N 15/00* | (2006.01) |
| *G01N 21/11* | (2006.01) |
| *G01N 21/64* | (2006.01) |

(52) U.S. Cl.
CPC ............. *C12Q 1/18* (2013.01); *G01J 3/0254* (2013.01); *G01J 3/433* (2013.01); *G01N 15/0205* (2013.01); *G01N 15/06* (2013.01); *G01N 21/031* (2013.01); *G01N 21/1717* (2013.01); *G01N 21/51* (2013.01); *G01N 21/53* (2013.01); *G01J 2003/4334* (2013.01); *G01N 21/11* (2013.01); *G01N 2015/0065* (2013.01); *G01N 2015/0222* (2013.01); *G01N 2015/0693* (2013.01); *G01N 2021/6469* (2013.01); *G01N 2021/6482* (2013.01); *G01N 2201/065* (2013.01); *G01N 2201/0642* (2013.01); *G01N 2201/06113* (2013.01)

(56) References Cited

U.S. PATENT DOCUMENTS

| | | | | |
|---|---|---|---|---|
| 3,772,154 | A | * 11/1973 | Isenberg | ............... G01N 35/028 435/286.4 |
| 3,983,006 | A | * 9/1976 | Acker | .................. G01N 21/253 435/33 |
| 4,076,420 | A | 2/1978 | De Maeyer et al. | |
| 4,416,995 | A | 11/1983 | Amaral | |
| 4,690,560 | A | 9/1987 | Coogan | |
| 4,942,305 | A | 7/1990 | Sommer | |
| 7,173,697 | B1 | 2/2007 | Moosmueller et al. | |
| 2002/0197740 | A1 | 12/2002 | Hansen et al. | |
| 2007/0146841 | A1 | 6/2007 | Moosmuller et al. | |
| 2008/0221711 | A1 | 9/2008 | Trainer | |
| 2010/0020323 | A1 | 1/2010 | Moosmuller et al. | |
| 2014/0240695 | A1 | 8/2014 | Pagan et al. | |
| 2018/0031472 | A1 | 2/2018 | Hammond et al. | |

FOREIGN PATENT DOCUMENTS

| | | |
|---|---|---|
| JP | S61-195685 | 8/1986 |
| JP | H05-113386 | 5/1993 |
| JP | 2002-522789 | 7/2002 |
| JP | 3304395 | 7/2002 |
| WO | WO 85/00426 | 1/1985 |
| WO | WO 00/10010 | 2/2000 |
| WO | WO 03/064991 | 8/2003 |
| WO | WO 2005/100955 | 10/2005 |

OTHER PUBLICATIONS

Masiyano et al. "Gas cells for tunable diode laser absorption spectroscopy employing optical diffusers. Part 2: Integrating spheres." Applied Physics B; Lasers and Optics, Springer, Berlin, DE, vol. 100, No. 2, Apr. 25, 2010, pp. 303-312, XP019845024.
Pickering et al. "Double-integrating-sphere system for measuring the optical properties of tissue," Applied Optics, Feb. 1993, vol. 32, No. 4, pp. 399-410.
Urban et al. "Characterization of Turbid Colloidal Suspensions Using Light Scattering Techniques Combined with Cross-Correlation Methods," Journal of Collid and Interface Science, Nov. 1998, vol. 207, No. 1, pp. 150-158.
Varma et al. "Toward an ideal integrating nephelometer," Optics Letters, Jun. 15, 2003, vol. 28, No. 12, pp. 1007-1009.
Search Report for United Kingdom Patent Application No. GB1502194. 2, dated Aug. 7, 2015, 6 pages.
International Search Report and Written Opinion prepared by the European Patent Office dated Apr. 22, 2016, for International Application No. PCT/GB2016/050319.
Brand et al. "Monitoring of microbial growth curves by laser nephelometry," BMG Labtech, 2004, 2 pages [found online at: www.bmglabtech.com/fileadmin/06_Support/Download_Documents/Application_Notes/AN125.pdf].
Official Action for New Zealand Patent Application No. 734187, dated Oct. 29, 2018, 4 pages.
Official Action for U.S. Appl. No. 15/549,507, dated Dec. 4, 2018 15 pages.
Official Action for European Patent Application No. 16704901.4, dated Sep. 18, 2019, 11 pages.
Official Action with English Translation for Japan Patent Application No. 2017-541953, dated Oct. 8, 2019, 7 pages.
Official Action for U.S. Appl. No. 15/549,507, dated May 16, 2019 12 pages.
Official Action for U.S. Appl. No. 15/549,507, dated Oct. 1, 2019 16 pages.

* cited by examiner (i) (ii)

(i) (ii)

Sample chamber 12

SCATTERED LIGHT INTEGRATING COLLECTOR

CROSS REFERENCE TO RELATED APPLICATIONS

This application is a continuation of U.S. patent application Ser. No. 15/549,507, filed Aug. 8, 2017, which is a national stage application under 35 U.S.C. 371 and claims the benefit of PCT Application No. PCT/GB2016/050319 having an international filing date of 10 Feb. 2016, which designated the United States, which PCT application claimed the benefit of Great Britain Application No. 1502194.2 filed 10 Feb. 2015, the entire disclosures of each of which are incorporated herein by reference.

The present invention relates to a device for measuring at least one property of a sample, for example a biological sample such as bacteria, using light.

BACKGROUND OF THE INVENTION

Classic spectrophotometers can be used to determine optical properties of bacteria using absorption or scattering. Absorption spectrophotometers can be used to measure the relative absorbance of a sample. Absorbance is measured by comparing the intensity of light entering a sample with the intensity of light exiting the sample. A drop in light intensity indicates a quantity of light has been absorbed. This can be displayed as an arbitrary figure, typically an optical density. This can lead to an accurate count of the number of cells present in a sample.

Scattering spectrophotometers usually comprise an intense light source, such as a laser or a very bright incandescent source, and a monochromator. Light is incident on a sample and is scattered at different angles. Detectors placed at discrete intervals around a chamber collect the scattered light. Collected light in the side scattering region can be used to obtain information about granularity and light collected in the forward scattering region can be used to obtain information about the size of the particles. Overall intensity of the scattered light gives a turbidity reading and an indication of the number of particles present. In scattering spectrophotometers for measuring bacteria, the typical wavelength of the light source is 600 nm. This wavelength is the most scattered and least absorbed by a number of organic materials, such as DNA, proteins, cytochromes.

Flow cytometers can also determine properties of a sample of interest. When a sheath-flow of index matched liquid flows through a narrow tube, the liquid acts to reduce the lumen of the tube forcing cells in the liquid to pass through the tube individually. This facilitates cell counting. Laser light incident on the narrow tube is scattered as individual cells pass through. Side and forward scattering data can be recorded to give information about the size and granularity of the cells under study. Thousands of cells can pass through the beam and be measured in this way in a few seconds and in very little liquid. Whilst cytometers are useful in some applications, they are sophisticated machines that require extensive training of an operator. Safe operation also requires a regular input of reagents and this contributes to on-going running costs. The interpretation of data produced can also prove challenging.

Another method for measuring concentration of suspended particles in a liquid or gas is nephelometry. Nephelometers can be configured to use integrating spheres. In such a configuration, light is incident on a sample and may be scattered by particles in the sample before entering the integrating sphere. The scattered light is then reflected and diffused inside the integrating sphere before being detected at an exit port of the sphere. Unscattered light passes straight through the sphere and is not collected.

SUMMARY OF THE INVENTION

According to one aspect of the present invention, there is provided a device comprising an integrating sphere light collector for collecting light and adapted to contain a sample within its internal volume in use. A sample holder may be provided to hold a sample inside the integrating sphere light collector. Typically, the sample comprises a fluid. Preferably a detector is provided on an internal surface of the integrating sphere light collector. A baffle may be positioned over the detector to prevent its direct illumination and ensure that only scattered and reflected light is incident on it.

By providing a sample holder that locates a sample inside an integrating sphere, highly sensitive measurements can be taken. This is because the hollow spherical cavity of the integrating sphere acts as a light diffusion and collection chamber. Light inside the cavity is reflected multiple times off the internal surface to produce a uniform distribution of light throughout the interior of the cavity. Because the sample is located inside the hollow spherical cavity, beams of light may pass through it multiple times.

The sample holder may comprise an internal volume of the integrating sphere. In this case, the internal volume is flooded with the sample and fulfils a dual purpose, i.e. to contain the sample and to act to diffuse and collect light. The sample may substantially fill the interior of the integrating sphere.

The integrating sphere light collector comprises an entry port for allowing light to enter the integrating sphere light collector and an exit port to allow unscattered light of the incident beam to exit the integrating sphere light collector.

The sample holder may be adapted to hold a sample substantially centrally within the integrating sphere light collector. The sample may be within a sample holder that extends along a diameter of the integrating sphere.

The sample holder may be adapted to hold a cuvette, for example a standard 10 mm length cuvette, in which a sample can be loaded. More specifically, the holder may be adapted to hold a cuvette of dimensions 45 mm×10 mm×10 mm (square footprint).

The sample holder may be a flow through holder for allowing a sample to flow through the integrating sphere light collector.

According to another aspect of the invention, there is provided a system for analysing a sample comprising: an integrating sphere light collector for collecting light and containing the sample; a light source for introducing light in the integrating sphere light collector; a signal generator for generating a control signal to cause the light source to output modulated light; a detector for detecting scattered light in the integrating sphere light collector and generating a signal indicative of the scattered light, and a lock-in amplifier operable to use a signal from the signal generator indicative of the light modulation and the signal generated by the detector to provide an output for analysis.

The light source may comprise a laser or a LED. The light source may be located in the integrating sphere light collector. The light source may be located external to the integrating sphere light collector. The light source may have a wavelength in the range of 590 nm to 650 nm, for example 635 nm. The light source may have a wavelength in the range of 620 nm to 750 nm, for example 635 nm.

According to yet another aspect of the present invention there is provided a device comprising an integrating sphere light collector for collecting light and containing a sample, and at least one light source and at least one detector on an internal surface of the integrating sphere light collector. The integrating sphere light collector may include a sample holder for containing the sample within its internal volume. The sample holder may be adapted to hold a sample substantially centrally within the integrating sphere light collector. The sample holder may be a flow through sample holder for allowing a sample to flow through the integrating sphere light collector. The sample holder may be adapted to hold a sample cuvette. The integrating sphere light collector may have an exit port to allow unscattered light to exit the integrating sphere light collector. Unscattered beam suppression means may be provided.

According to still another aspect of the present invention, there is provided a device comprising an integrating sphere light collector for collecting light and for containing a sample, and a pipette tip, wherein the integrating sphere light collector is at one end of the pipette tip and the pipette tip is arranged to draw a sample fluid into the integrating sphere light collector.

According to still another aspect of the present invention, there is provided a method for monitoring drug susceptibility of a biological sample, the method comprising: introducing the biological sample into an integrating sphere light collector; introducing a drug into the biological sample; introducing light into the integrating sphere light collector, so that the light passes through and is scattered by the sample; detecting scattered light in the integrating sphere light collector; repeating the steps of emitting and detecting as a function of time and analysing the detected light to determine drug susceptibility. The sample may comprise a species or strain of bacteria/fungi. Analysing the captured light may involve establishing the level of drug that kills or inhibits growth of a given organism. The method may involve monitoring an undosed biological sample at the same time as the drugged sample.

According to still another aspect of the present invention, there is provided a method for counting cells, the method comprising: introducing a sample into an integrating sphere light collector; emitting light in the integrating sphere light collector, so that the light passes through and is scattered by the sample; detecting scattered light in the integrating sphere light collector; and analysing the detected light to determine the number of cells.

According to still another aspect of the present invention, there is provided a method for determining a cell state of a bacterial culture, the method comprising: introducing a bacterial culture sample into an integrating sphere light collector; emitting light in the integrating sphere light collector, so that the light passes through and is scattered by the sample; detecting scattered light in the integrating sphere light collector; and analysing the detected light to determine the number of cells, wherein changes in the detected light as a function of time are indicative of a change in cell state.

According to still another aspect of the present invention, there is provided a method for monitoring a biological material, the method comprising: introducing a biological sample into an integrating sphere light collector; emitting light in the integrating sphere light collector, so that the light passes through and is scattered by the sample; detecting scattered light in the integrating sphere light collector; and analysing the detected light, wherein changes in the captured light as a function of time are indicative of a change in the biological material. The change in the biological material may be a change in cell state.

The biological material may include a pathogen and the change in the biological material may be a change in a level or concentration of the pathogen, thereby indicating growth of that pathogen.

The biological material may include a microbe and the change in the biological material may be a change in a level or concentration of the microbe, thereby indicating growth of that microbe.

BRIEF DESCRIPTION OF THE DRAWINGS

Various aspects of the invention will now be described by way of example only, and with reference to the accompanying drawings, of which.

DETAILED DESCRIPTION OF THE DRAWINGS

Figure 1:
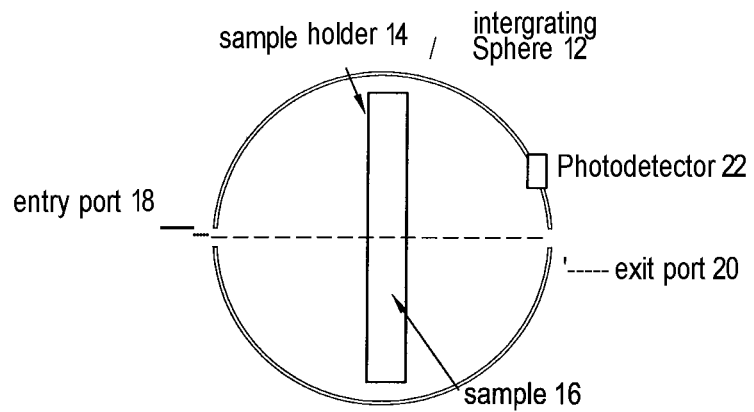
FIG. 1 is schematic representation of an integrating sphere light collector for measuring optical properties of a sample, and in particular a biological sample.

FIG. 1 shows a scattered light integrating collector 10. The collector 10 has an integrating sphere 12 and a sample holder 14 for holding a sample within the integrating sphere 12. In the example shown in FIG. 1, the sample holder 14 is adapted to hold a sample cuvette 16 within the sphere 12.

The integrating sphere 12 has a hollow spherical cavity, an entry port 18 and an exit port 20. The entry port 18 and exit port 20 define the end points of an optical path through the hollow spherical cavity. The entry and exit ports 18 and 20 respectively are positioned on opposing sides of the spherical cavity. An internal surface of the hollow spherical cavity is diffusive and so capable of reflecting and diffusing light. In some cases, a thin aluminium or silver coating is applied to an inner surface of the sphere and covered with a layer of titanium oxide II paint. These layers reflect back any laser radiation that was scattered by the sample and diffuse any light that was scattered by the sample and reaches the inner face of the sphere, respectively.

The sample holder 14 and sample cuvette 16 are positioned so that in use the sample extends across substantially the entire diameter of the integrating sphere 12. This helps maximise the volume of the sample that can interact with reflected and diffused light circulating within the sphere.

On the internal surface a photodetector 22 is provided, for example a photodiode. This is used to measure the intensity of light in the cavity as a function of time. A baffle is positioned over the photodiode to prevent its direct illumination and ensure that only scattered and reflected light is incident on it, thereby increasing the quality of the signal.

Light enters the hollow spherical cavity of the integrating sphere 12 through the entry point 18. The hollow cavity acts as a light diffusion and collection chamber. Light inside the cavity is reflected multiple times off the internal surface of the hollow cavity to produce a uniform distribution of light throughout the interior of the cavity. Unscattered light exits the hollow cavity through the exit port 20 to a beam dump. Scattered light is measured by the photodetector 22. Because the sample is located inside the hollow spherical cavity, beams of light may pass through it multiple times. This results in highly sensitive measurements.

Figure 2:
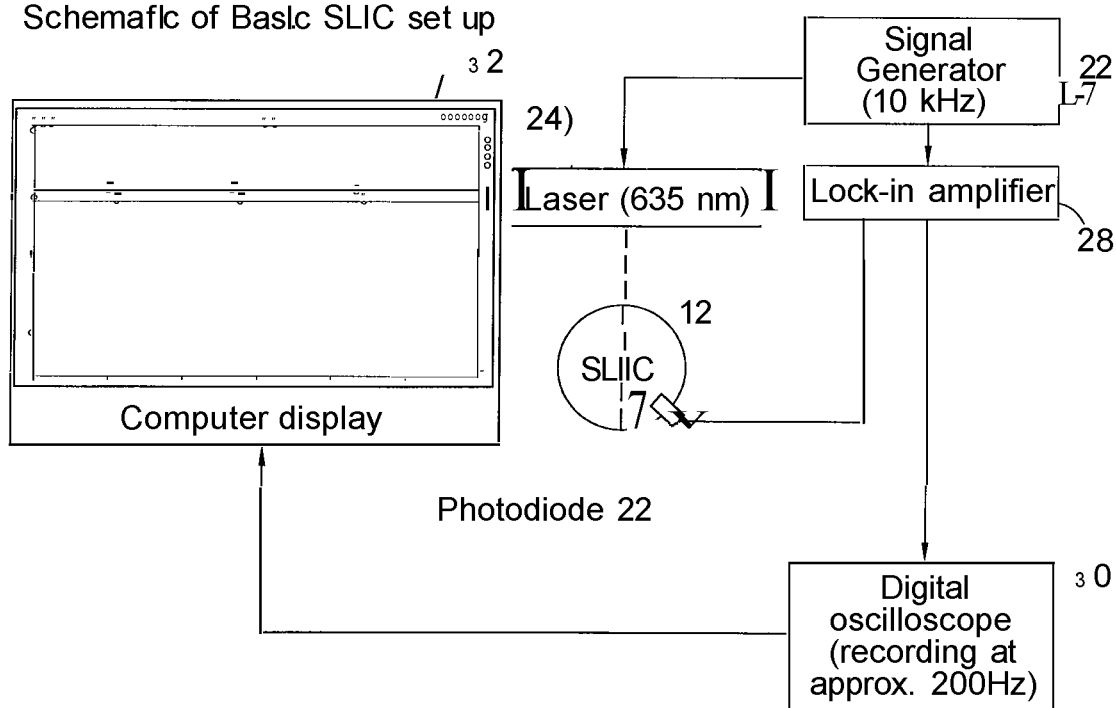
FIG. 2 is a block diagram of a detection and analysis system for use with the integrating sphere light collector of FIG. 1.

FIG. 2 shows a detection and analysis system for use with the collector of FIG. 1. At the input port 18 of the collector is a light source 24, for example is a 635 nm wavelength laser (although any red light in the wavelength 620-750 nm could be used), for inputting light to the integrating sphere 12. The laser 24 is connected to a signal generator 26 that is adapted to control a modulation frequency and phase of the laser output. The photodiode 22 is connected to a lock-in amplifier 28. An input of the amplifier 28 is connected to the signal generator 26. An output of the amplifier 28 is connected to a digital oscilloscope 30. The lock-in amplifier 28 uses phase-sensitive detection to single out a component of the signal at a specific reference frequency and phase, in this case the modulation frequency that is set by the signal generator. Noise signals, at frequencies other than the reference frequency, are rejected and do not affect the measurement. An output from the digital oscilloscope 30 is fed to a computer display 32.

The signal generator 26 is arranged to modulate the output frequency of the laser source 24. As an example, the laser may be modulated at a frequency of 10 kHz with a phase of +169°, and a peak-to-peak amplitude of 200 mV. The detected signal is filtered by the lock-in amplifier 28. The lock-in amplifier 28 filters the detected signal from the photodiode 22. The lock-in amplifier 28 synchronizes the detected signal with the modulation applied to the light source 24 to provide a dampening system that eliminates unwanted noise, for example, background electrical or luminous noise. The filtered signal is sent to the digital oscilloscope 30 to be recorded. The recorded signal can be displayed on the computer display 32.

Raw data is collected by the digital oscilloscope. Typically around 16,000 data points are collected for every 30 second experiment. The data is exported to a calculation suite in a processor which returns the averages (mean, median, mode) and the standard deviation of the data points. If the standard deviation is above a threshold (indicating aberrations from the norm in the data) the data is discarded. The mean of each experiment is selected. The experiments have between 3 and 89 technical replicates, which are collected and tabulated. The standard error from the mean of these averages is calculated and charted as error bars along with the data. Once the data is graphed, a function, such as a standard Gompertz, is fitted to the data in order to estimate future outcomes of experiments such as inocula sizes.

In use, a sample is placed inside the sample cuvette 16 and positioned in the sample holder 14, which holds the sample in the interior of the hollow cavity. Incoming light from the source 24 enters the cavity through the entry port 18. The sample is positioned such that the incoming light beam is incident on the sample. Incoming light may be scattered by the sample. The scattered light is then reflected, multiple times, by the internal surface of the cavity. The hollow cavity acts as an integrating sphere and integrates or adds up the reflected light inside the sphere. The sum of the diffused light is sampled by the photodiode 22. This is done as a function of time. Unscattered light travels straight through the cavity and is absorbed by a beam dump or a baffle.

Due to the geometry and scattering properties of the internal surface of the hollow cavity of the integrating sphere 12 reflected light is incident on the sample from all directions. With a sample present inside the hollow cavity, the distribution of the light detected by the photodetector 22 will change dependent on the optical properties of the sample.

Various different embodiments of the integrating sphere 12 with its internal sample arrangement will now be described.

Figure 3A:
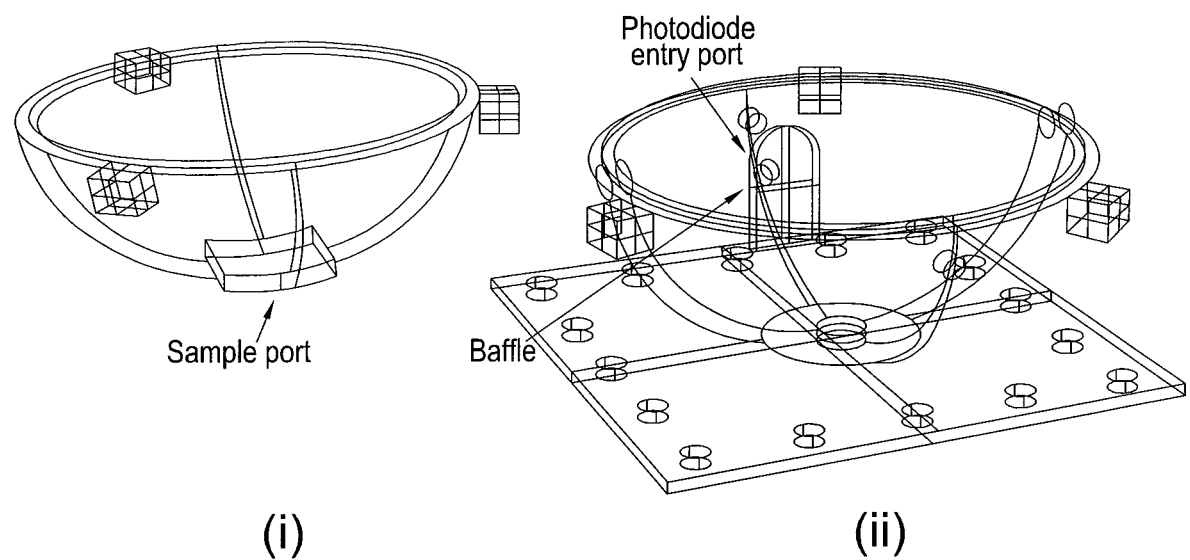
FIGS. 3(a) and (b) show various parts of a first example integrating sphere light collector and sample holder.
Figure 3B:
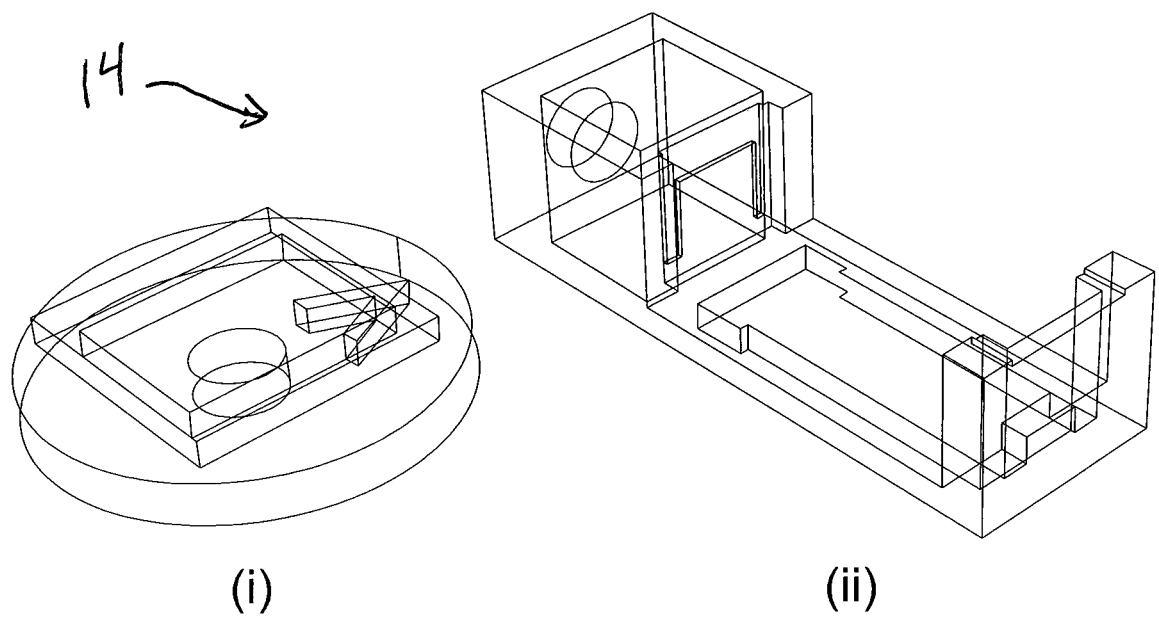

FIG. 3(*a*) shows two parts that make up the spherical portion of a collector. FIG. 3(*a*)(*i*) shows an upper part of the collector with an upper hemisphere. The upper part of the collector has a sample port for receiving a sample holder. FIG. 3(*a*)(*ii*) shows a lower part of the collector which has a base and a lower hemisphere. In this part, a port is provided for holding a photodiode. This is positioned behind a baffle, so that only scattered or reflected light is transmitted to the photodiode. FIG. 3(*b*) shows two parts of a sample holder for inserting in the sample port of FIG. 3(*a*)(*i*). The sample holder has a lid and a body for holding the sample, and in particular in this case, a sample cuvette. When assembled the sample body is designed to hold the sample at the centre of the collector. The lid and body connect together to form a sample holder. The integrating sphere is formed by connecting the upper and lower hemispheres of FIG. 3(*a*). A sample is loaded into the sample holder, which is then loaded into the sample port of the collector. The sample holder holds the sample in the centre of the collector. The lid of the sample holder completes the sphere of the collector.

Figure 4A:
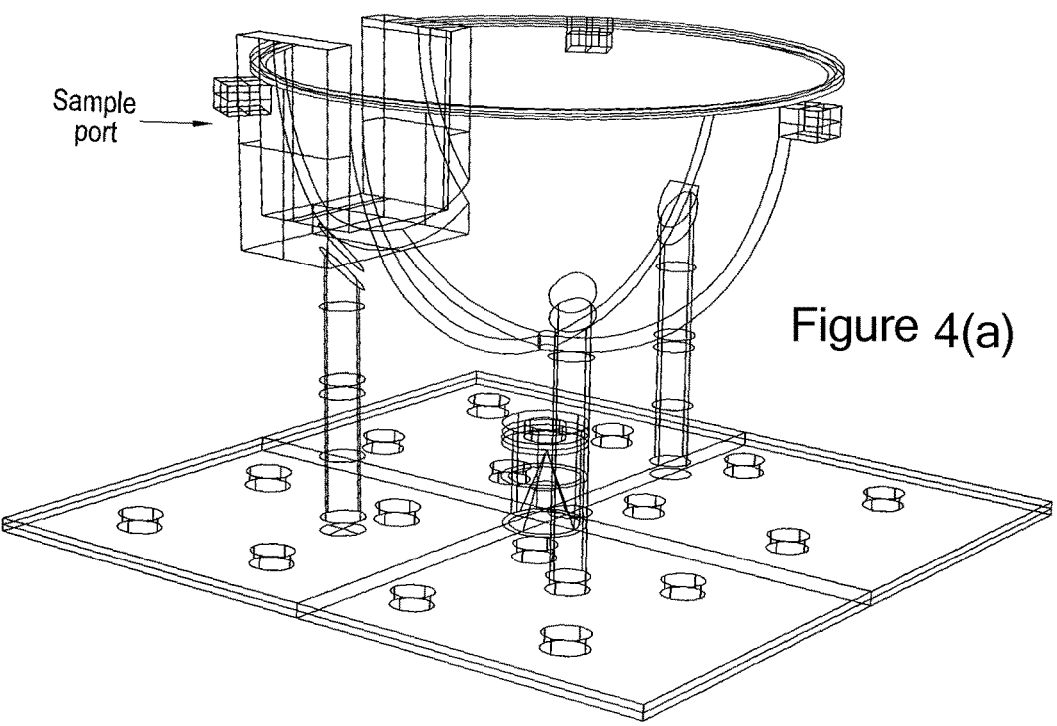
FIGS. 4(a) to (c) show various parts of a second example integrating sphere light collector and sample holder.
Figure 4B:
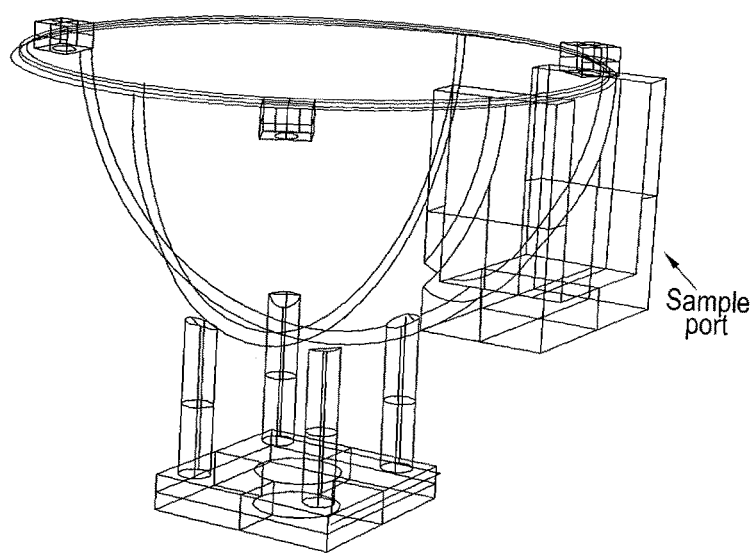
Figure 4C:
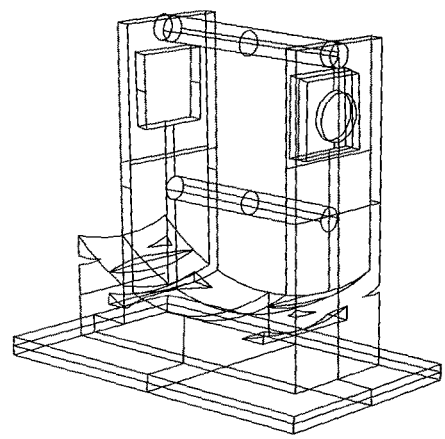

FIGS. 4(*a*), 4(*b*) and 4(*c*) show parts of another example collector. FIG. 4(*a*) shows a lower half of a collector. The lower half is a hemisphere modified to contain part of a sample port. FIG. 4(*b*) shows the upper half of the collector. FIG. 4(*c*) shows a sample holder. The sample holder has a curved surface that completes the interior of the collector when assembled. In use, the two halves of the collector are connected together leaving an open sample port. The sample holder of FIG. 4(*c*) is then inserted into the sample port, which completes the integrating sphere and locates the sample in a central position inside the sphere.

Figure 5A:
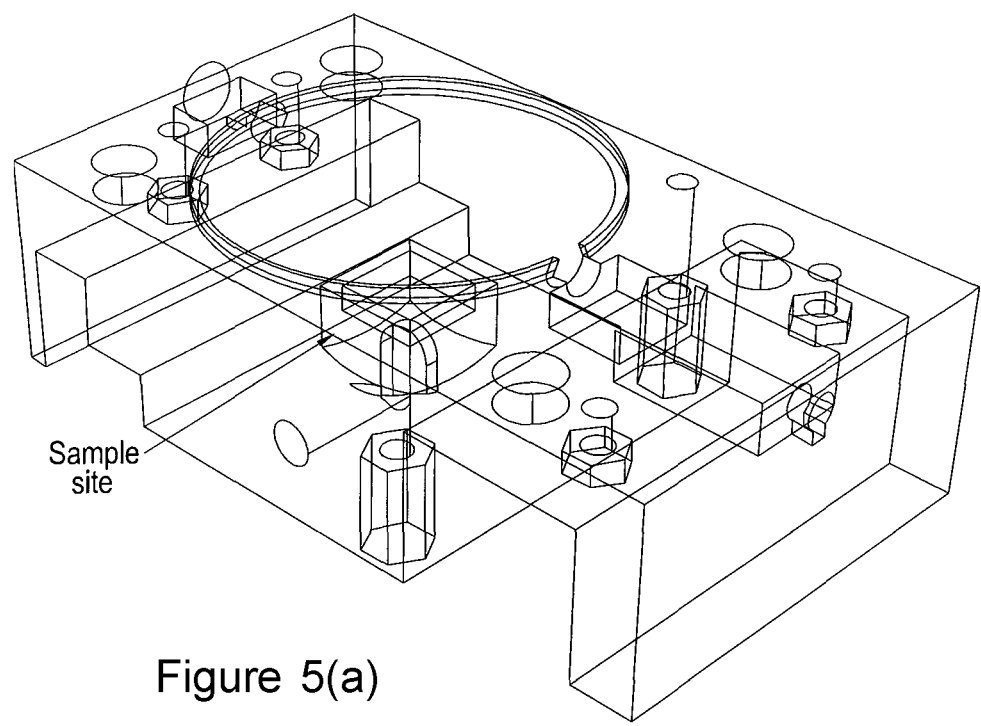
FIGS. 5(a) to (c) show various parts of a third example integrating sphere light collector and sample holder.
Figure 5B:
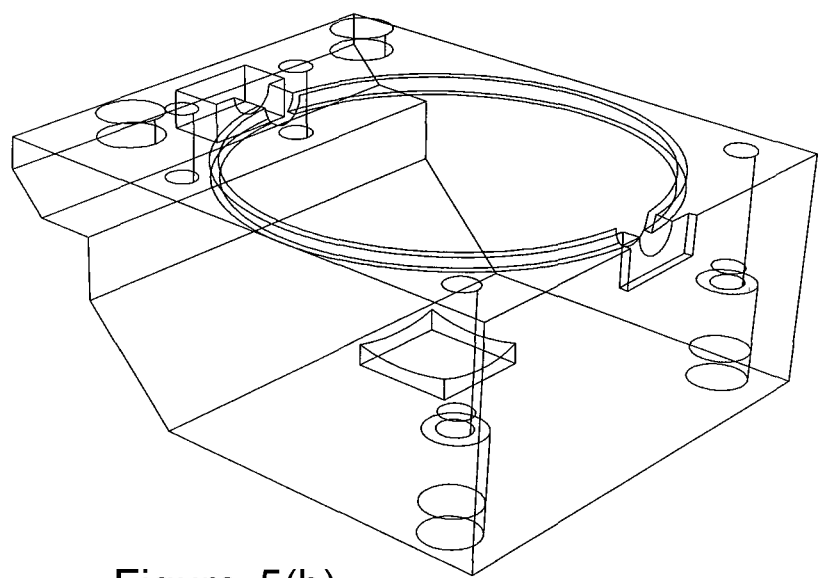
Figure 5C:
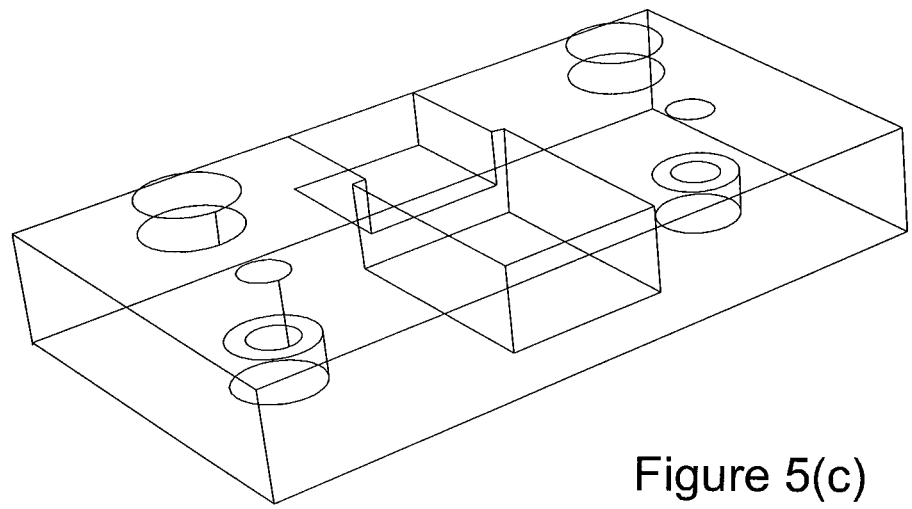

FIGS. 5(*a*), 5(*b*) and 5(*c*) show parts of yet another example collector. In this case, the collector is formed from blocks of material with hollowed out cavities. FIG. 5(*a*) shows a lower block. The lower block has a hollow hemispherical cavity formed in it, and a sample site located at the base of the cavity. The lower block is adapted to house a laser. FIG. 5(*b*) shows the upper block. The upper block has a hollow hemispherical cavity formed in it. FIG. 5(*c*) shows a laser casing for connecting to the lower block. In use, a sample is loaded on to the sample site. The upper block is then attached thus completing a hollow spherical cavity. The laser casing is removed from the lower block only for maintenance of the laser.

In all of the examples described with reference to FIGS. 3 to 5, the sample holder is designed to minimise interference with the light circulating in the sphere. For example, the sample holder may be made of a material substantially transparent at the wavelength of operation.

Figure 6:
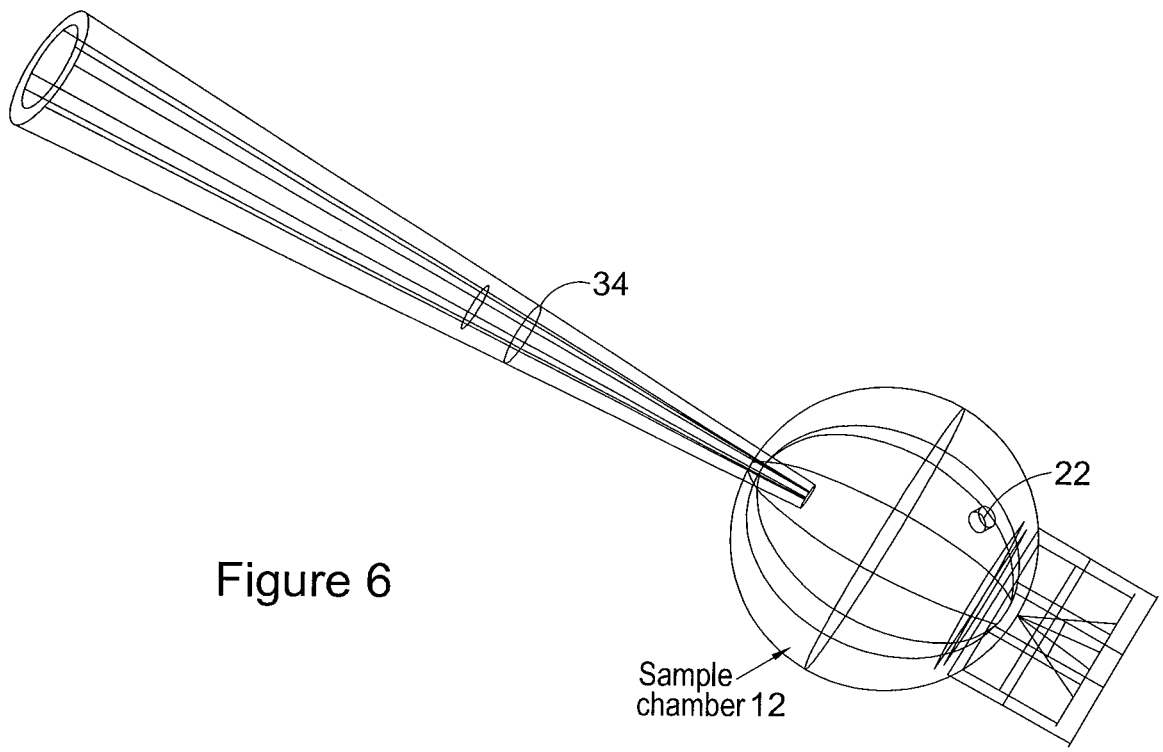
FIG. 6 is a schematic representation of a fourth example integrating sphere light collector.

FIG. 6 show a pipette-like device that incorporates a spherical collector. The spherical collector is an integrating sphere 12 as described above. The device has a pipette tip 34 and a collector 12. The pipette tip 34 is disposable. As before, in the wall of the collector is a photodiode 22. The interior of the spherical collector acts as a sample chamber. In use, a sample is drawn up through the pipette tip 34 by a pipette mechanism. The sample is drawn into the sample chamber, so that the interior of the spherical collector is flooded with the sample. Once the sample is present inside the spherical collector, a laser can be activated. Light scattered by the sample, and reflected by the collector is then detected by the photodiode 22 embedded in the wall. After a reading is made, the contaminated device can be disposed.

The device of the invention can be used to determine bacterial susceptibilities to drugs. This is done over time with a set concentration of drug. To do this, bacterial species are measured and diluted or concentrated to a clinically significant level. A quantity of drug that the bacteria are susceptible to is added at a concentration greater than the accepted MIC (minimum inhibitory concentration). The dosed culture is grown at accepted conditions in parallel with another culture that has been treated identically with the exclusion of the drug. The diluent used for the drug (PBS or water) is added at the same volume as the drug in the dosed culture. At predetermined time points, the cultures are removed from the incubator and measured in the integrated collector in 1 ml cuvettes. The first time point at which there is a statistically significant difference between the dosed and the free-growing cultures is declared the time to positivity (TTP). Tests have demonstrated that the system of the invention has a TTP faster than any other drug susceptibility apparatus on the market.

Various drug susceptibility experiments have been conducted. For these, the collector of FIG. 3 was used. The oscilloscope used was a picoscope 4226 with picoscope software to translate the raw data. The light source used was a modulated diode laser with a well-defined output wavelength of 635 nm. The scan rates for the oscilloscope (which is the rate limiting stage) are around 200 Hz. It is set to take a measurement every millisecond (1 kHz). However, the processor used limited the average amount of data to around 1600 data points per 30 second experiment. This works out at 0.01875 measurements per second or around 200 Hz. Data from the oscilloscope is imported into data handling software (e.g. excel, R, SPSS, matlab) and the average of the ~1600 data points from the 30 second scan is calculated. The standard deviation and/or standard error can be calculated and used to show the stability of the signal during the scan.

Figure 7:
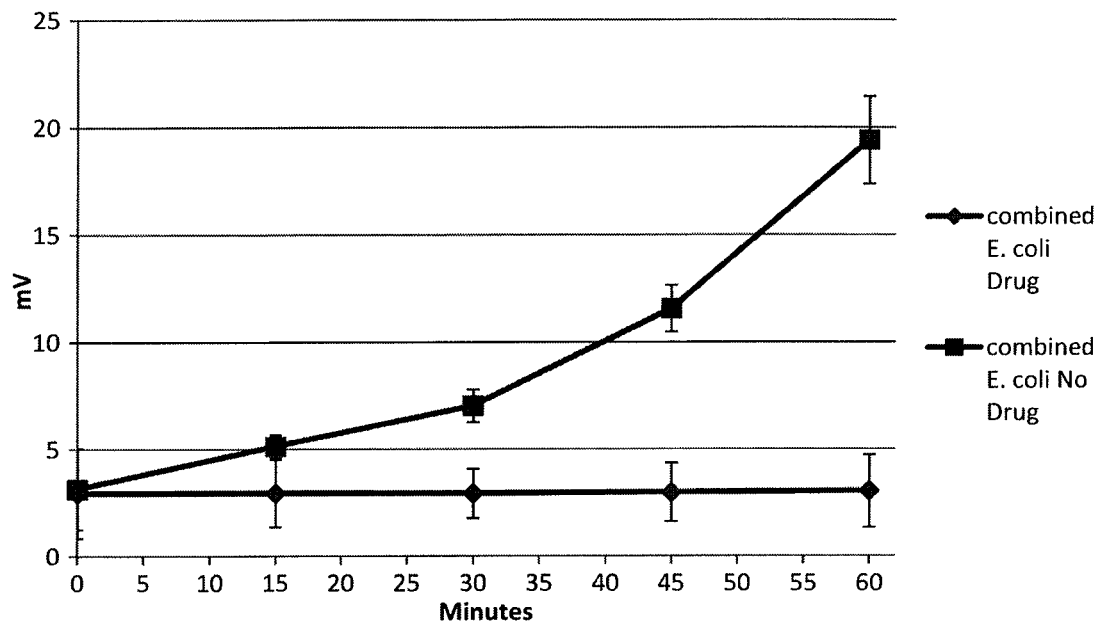
FIG. 7 is a plot of detector output as a function of time for two E. coli samples, one with a drug and one without.

FIG. 7 is a graph of detector output (in mV) as a function of time for two *E. coli* samples, one with a drug and one without, from three separate experiments in which triplicates of each sample were run (n=9). Error bars are plus and minus one standard error from the mean. The blue line indicates the sample in which 20 µg/ml of ciprofloxacin was added prior to inoculation with bacteria. Bacteria were added at levels under the detection limit of a Shimadzu UV-1601 UV-Vis spectrophotometer and later quantified by CFU count as between 300-700 cells/ml across all experiments. The red line indicates the sample that had no drug added and was allowed to grow normally with the same number of bacteria added at the same time point. Cultures were incubated at 37° C. shaking at 210 RPM between sampling and sampling was limited to between 3-5 minutes to arrest any loss of heat from the samples so as to not greatly affect their growth times. Statistical tests (T test and Chi squared) indicate the 30-minute time point to be first point at which there is a significant difference between the two samples. Therefore, 30 minutes is the detection time.

TABLE 2

Chi squared and T-test results for all time points in FIG. 7.

| | minutes | | | | |
|---|---|---|---|---|---|
| | 0 | 15 | 30 | 45 | 60 |
| Chi$^2$ | 0.934147 | 0.180333 | 0.024681 | 6.5E−05 | 9.33E−10 |
| T-test | 0.207025 | 0.034152 | 0.004411 | 0.000271 | 0.002039 |

Figure 8:
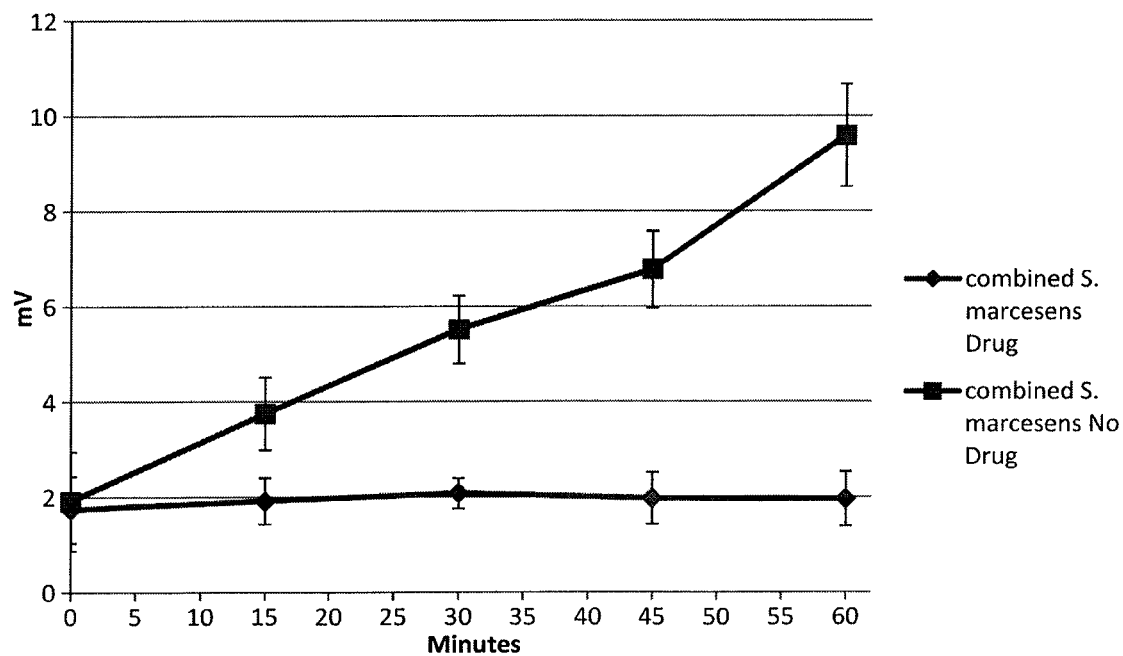
FIG. 8 is a plot of detector output as a function of time for two S. marcescens samples, one with a drug and one without.

FIG. 8 is plot of detector output (in mV) as a function of time for two *S. macresens* samples, one with a drug and one without, from three separate experiments in which triplicates of each sample were run (n=9). Error bars are standard error from the mean. The blue line indicates the sample in which 20 µg/ml of ciprofloxacin was added prior to inoculation with bacteria. Bacteria were added at levels under the detection limit of a Shimadzu UV-1601 UV-Vis spectrophotometer and later quantified by CFU count as between 300-700 cells/ml across all experiments. The red line indicates the sample that had no drug added and was allowed to grow normally with the same number of bacteria added at the same time point. Cultures were incubated at 37° C. shaking at 210 RPM between sampling and sampling was limited to between 3-5 minutes to arrest any loss of heat from the samples so as to not greatly affect their growth times. Statistical tests (t-test and Chi squared) indicate the 30 minute time point to be first point at which there is a significant difference between the two samples. Therefore, 30 minutes is the detection time.

TABLE 3

Chi squared and T-test results for all time points in FIG. 8.

| | minutes | | | | |
|---|---|---|---|---|---|
| | 0 | 15 | 30 | 45 | 60 |
| Chi$^2$ | 0.835984 | 0.239163 | 0.039273 | 0.005643 | 0.000106 |
| T-Test | 0.298238 | 0.03116 | 0.007687 | 0.010741 | 0.006206 |

Figure 9:
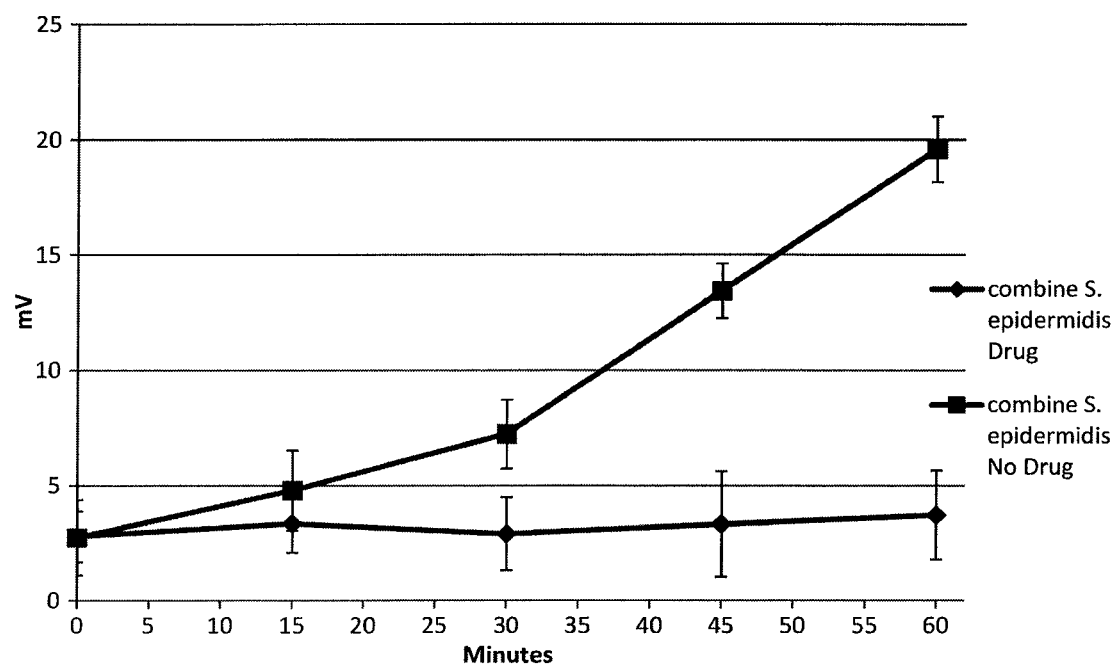
FIG. 9 is a plot of detector output as a function of time for two S. epidermidis samples, one with a drug and one without.

FIG. 9 is a plot of detector output as a function of time for two *S. epidermidis* samples, one with a drug and one without, from three separate experiments in which triplicates of each sample were run (n=9). Error bars are standard error from the mean. The blue line indicates the sample in which 20 µg/ml of ciprofloxacin was added prior to inoculation with bacteria. Bacteria were added at levels under the detection limit of a Shimadzu UV-1601 UV-Vis spectrophotometer and later quantified by CFU count as between 300-700 cells/ml across all experiments. The red line indicates the sample that had no drug added and was allowed to grow normally with the same number of bacteria added at the same time point. Cultures were incubated at 37° C. shaking at 210 RPM between sampling and sampling was limited to between 3-5 minutes to arrest any loss of heat from the samples so as to not greatly affect their growth times. Statistical tests (T test and Chi squared) indicate the 30-minute time point to be first point at which there is a significant difference between the two samples. Therefore, 30 minutes is the detection time.

TABLE 4

Chi squared and T-test results for all time points in FIG. 9.

| | minutes | | | | |
|---|---|---|---|---|---|
| | 0 | 15 | 30 | 45 | 60 |
| Chi$^2$ | 0.893886 | 0.520936 | 0.017505 | 8.32E−06 | 3.71E−09 |
| T-test | 0.445398 | 0.019607 | 0.001156 | 0.020599 | 0.012607 |

FIGS. 7 to 9 indicate that at 30 minutes there is a significant difference between the sample dosed with ciprofloxacin and the one allowed to grow normally. A detection time of 30 minutes is a significant improvement on the detection times of known technology.

The experiments described above may be extended for a clinical lab to allow many samples to be tested simultaneously. Cultures with suspected bacterial growth (blood samples from sepsis for example) need simply be loaded into blood incubator tubes (as is done now in hospitals) and have suspected efficacious drugs added, one to each tube totalling, for example, 20 tubes plus one control with no drug. These would all then be grown as is current standard procedure with samples removed and analysed by SLIC every 15-30 minutes until it is clear which drugs are effective in retarding growth of the bacteria relative to the control.

In the experiments described above, the sample is held within a constant volume sample container, i.e. a sample cuvette. It will be appreciated that the invention can be used in a constant flow system. For example, a flow cuvette may be placed in the spherical collector with feeding and draining tubes attached. A bacterial culture may be passed through the cuvette by gravity pumping from a heated reservoir and measurements taken constantly.

For a flow based system, the flow rate has to be controlled to ensure that sufficient samples can be taken. The flow rate can be determined using:

flow rate=¼×π×(pipeline diameter)$^2$×velocity
velocity=sampling rate×beam volume Using the oscilloscope and processor described above, with the measurement frequency of 200 Hz, a flow pipeline diameter of 10 mm and a beam volume of 30 mm$^3$, a flow system would require the flow rate to be limited to ~470 ml/s (roughly half a litre per second). A faster processor would speed up this system considerably.

Real-time growth curves can be collected using the device of the invention. In this case, the device would be placed in an incubator with a static or flowing culture vessel within it. Data would be collected over time, so that a sample could be measured for turbidity at any time point required. Indeed, the measurements could be taken multiple times per minute or continuously.

Figure 10:
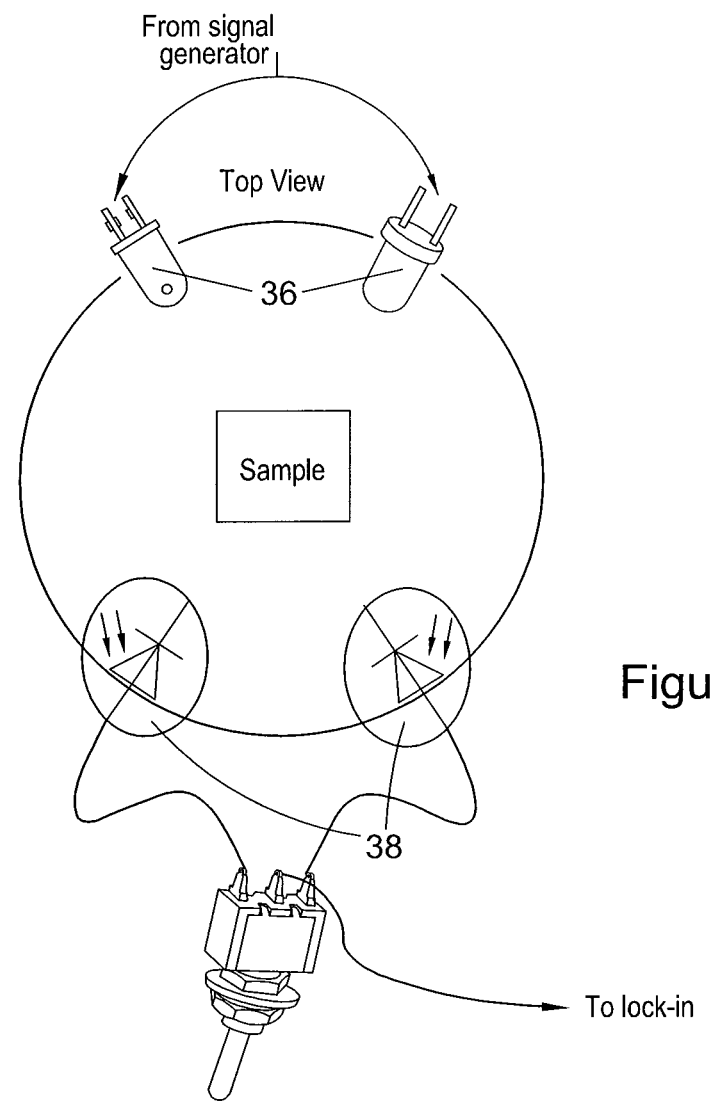
FIG. 10 is a top view of an integrating sphere light collector with internal light sources.

FIG. 10 shows another embodiment of the invention. In this case, the device is adapted to perform fluorescence measurements using at least one light source and at least one detector mounted inside the integrating sphere, the at least one light source being operable to emit light of at least one wavelength suitable for stimulating fluorescence and the at least one detector being operable to detect the emitted fluorescence. For fluorescence measurements, the whole sample has to be illuminated and there is no need for a light exit port. To ensure that only fluorescence is detected a combination of a photodiode and an optical shield/filter may be used as the detector. The shields may be moulded from optical quality plastics at a specific wavelength bandpass.

FIG. 10 shows two light sources 36, in this case LEDs, and two associated light detectors 38, in this case photodiodes, are provided on an internal surface of an integrating sphere light collector. The light source(s) 36 emit at a wavelength matched to the absorption wavelength(s) of the material(s) of interest. The photodiodes 38 have peak sensitivity at the expected fluorescence emission range.

Figure 11:
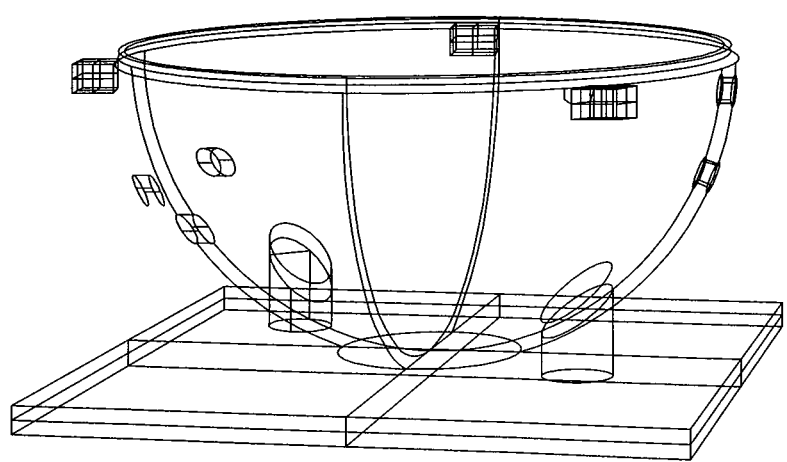
FIG. 11 is a perspective view of a lower half of the integrating sphere light collector of FIG. 10.

FIG. 11 shows a 3D rendering of the bottom half of a sphere that can be used to produce a physical 3D device using for example 3D printing techniques. The wavelength of light emitted by the LEDs is selected to stimulate fluorescence of a material of interest.

Fluorescence measurements have been taken. The wavelengths used were blue-430±30 nm and green-525±15 nm. The LEDs were driven directly from the signal generator (no other power input required) and oscillated at 10 kHz and 200 mV amplitude, peak to peak. Fluorescence signal interference was detected via custom photodiode shields and photodiodes that have peak sensitivity at the expected emission range(s). Differentiation of fluorescence measurements versus background versus environmental illumination are dealt with by a combination of the custom coloured shields and the fact that the LEDs and photodiodes are housed on the inner face of the integrating sphere. In this example, the shield used on one photodiode was green (525±15 nm) and on the other photodiode the shield used was red (630±18 nm). These shields were selected to allow detection of the fluorescence output of the stain nile red when it is exposed to a lipid rich environment.

Whilst the integrating spheres of FIGS. 10 and 11 are shown with only internal light sources, they could be combined with the arrangement of FIG. 1, so that internal and external sources could be used. Preferably, the internal sources are used for fluorescence measurements, as described above. Preferably, the external source is used for other optical measurements, as described above.

The present invention has numerous applications. For example, the invention can be used to establish early growth of pathogens in human/animal/food samples or on medical devices such as drips. It can also be used to detect minute changes in cellular concentrations in chemotherapy studies for microbiology/oncology/mycology or to detect impurities in water or other fluids.

As another example, the invention can be used for simple cell counting. Enumerating the number of cells in a sample is a common microbiological task and the invention makes it simple, rapid and easy and with the possibility of an operator being able to build a database of their own cells in a particular medium to allow for the rapid detection of small changes in a sample, such as a burgeoning contamination or a small colour change in the medium. Using the invention the number of bacteria in a sample can be determined with precision down to a lower limit of ~10 microbes per mL.

The invention is sensitive enough to be able to differentiate between cultures with very similar cell numbers. In particular, the invention allows for rapid drug susceptibility testing of species or strains of bacteria/fungi to establish the level of drug which will kill or inhibit growth of a given organism. For example, small shifts in cell number early in drug susceptibility studies can be detected where one culture has been dosed with a bacteriostatic concentration of an antibiotic and another is allowed to replicate naturally (as demonstrated above with reference to FIGS. 7 to 9).

The invention could also be useful in determining the cell state of a bacterial culture. This is because some microbes change their morphologies under different circumstances, and different sizes and shapes of bacteria will scatter light differently. Equally, MIC (minimum inhibitory concentration—the smallest amount of a given drug that will inhibit the growth of a given bacterial species of strain)/MBC (minimum bactericidal concentration—the smallest amount of a given drug that will kill all present cells of a given bacterial species of strain in a sample) breakpoint analysis can be done to establish the point at which a microbial strain is or is not responding to a particular antibiotic or combination of antibiotics.

In yet another application, the growth of microbes in a non-opaque media can be tracked. This can be done in a range from the lower detection limit (<10 microbes per mL) to ~$10^9$ microbes per mL as a function of time. This can be automatic at distinct time intervals or manual at the operator's discretion, or a combination of the two.

Using post-acquisition data analysis the growth rate of microbial samples can be determined, i.e. the time it takes for bacteria to divide. Also in certain assays (e.g. drug susceptibility) the number of bacteria can be estimated. This is done using an automated analysis and so can provide systematic computation without user input into the analysis.

Figure 12:
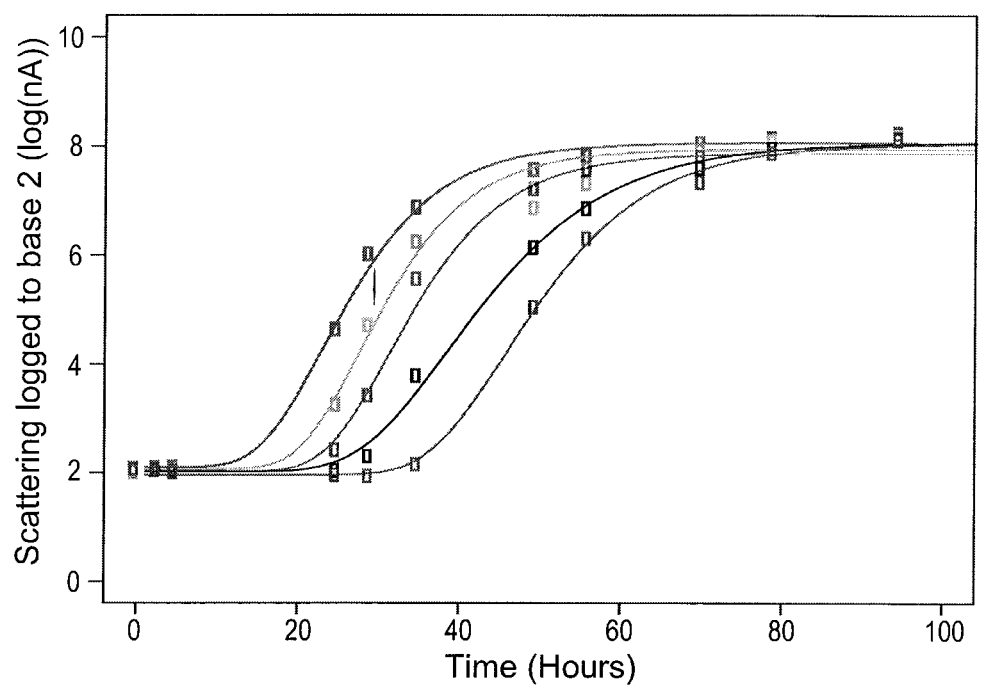
FIG. 12 is a logarithmic plot of scattering intensity as a function of time for different sample dilutions.
Figure 13:
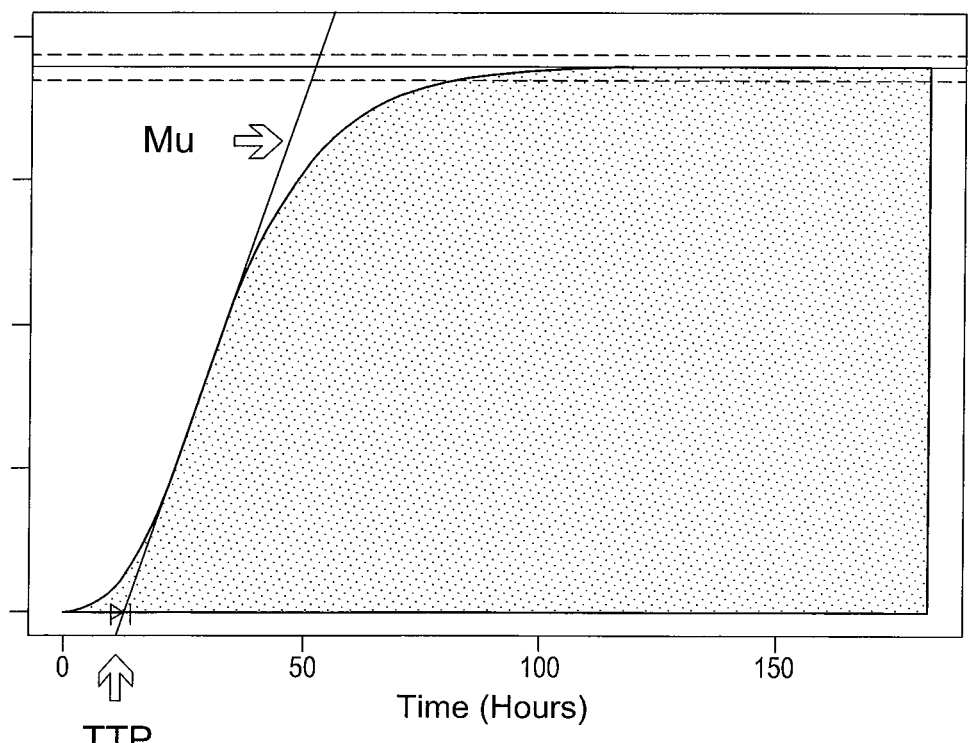
FIG. 13 is a logarithmic plot of scattering intensity as a function of time for a single sample on which Mu is shown.

As an example, FIG. 12 shows growth curves from *M. smegmatis*. In FIG. 12, the different curves represent different dilutions. The circles represent the raw data points. The solid line represents the fitted gompertz function. The Y axis is the log base 2 of the value of the scattering intensity. FIG. 13 is an example of a fitted gompertz function. Mu is the gradient at the steepest part of the curve. Time to positivity (TTP) is where this line intercepts the x-axis. Mu is used to calculate the growth rate of the bacterium. TTP is used to calculate the number of bacteria.

Figure 14:
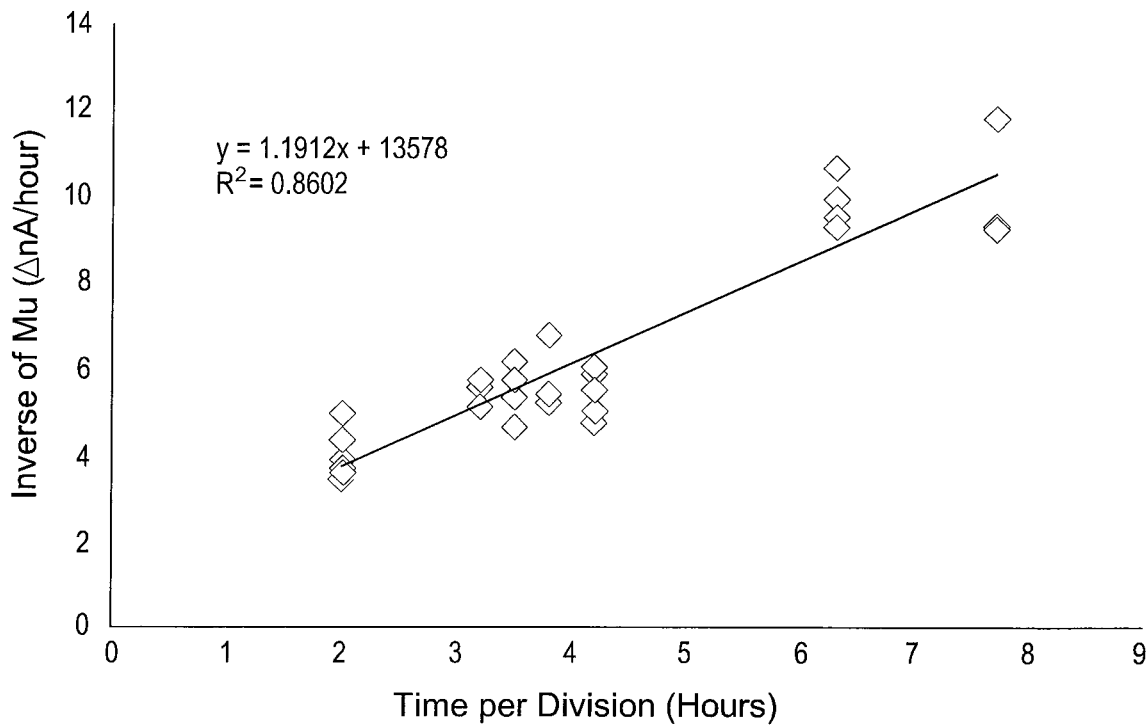
FIG. 14 is a plot of the inverse of Mu as a function of per division of bacteria.

FIG. 14 shows the relationship between 1 over Mu (the steepest part of the gompertz function) and the time it takes for the bacteria to divide. This allows for conversion between the Mu value from the gompertz curve and an estimate of the time it takes the bacteria to divide. The relationship between Mu and the Time per generation/division can be expressed as:

estimate of time per division=−1.37578/Mu*1.1912

Hence, by measuring Mu, an estimate of the time per division can be estimated.

Using the above equation, it can be shown that:

Number of division till positivity=TTP/Estimate of time per division.

Figure 15:
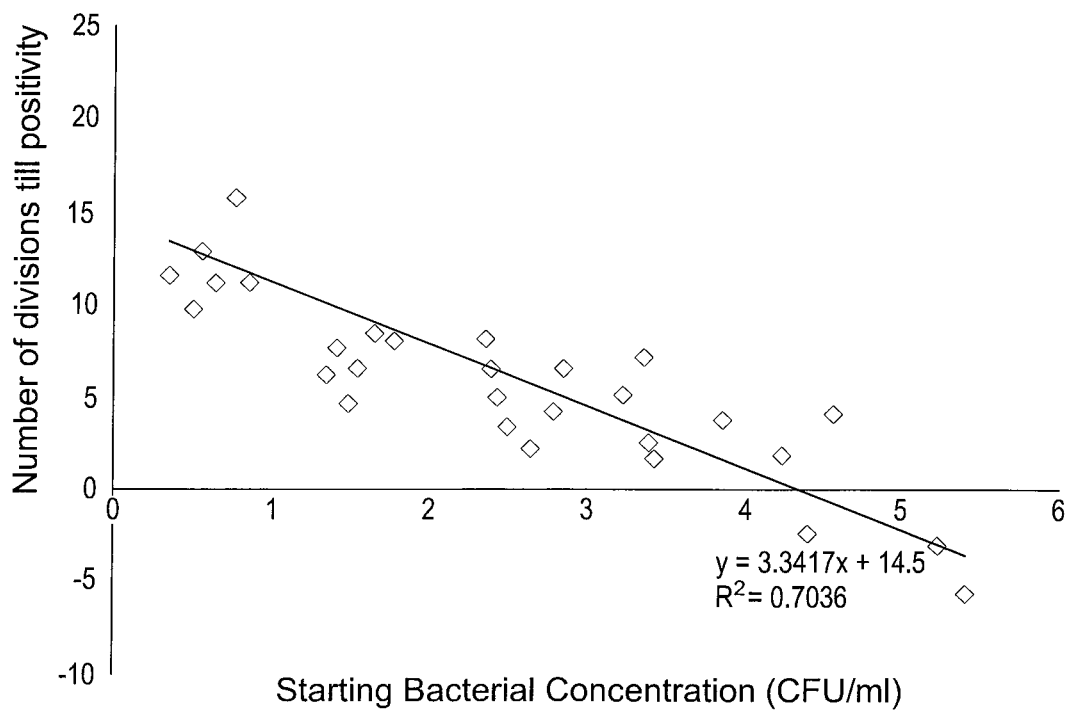
FIG. 15 is a plot "number of divisions till positivity" vs number of cells in a sample at a measurement start point.

FIG. 15 is a plot of "Number of divisions till positivity" vs number of cells that were in the sample at the start as derived by CFUs (colony forming units). FIG. 15 applies to cultures that only have exponential growth, i.e. they have no lag phase. The when the time to positivity is divided by the estimated time per division (as derived in FIG. 14) the result is the number of divisions to positivity. This is represented on the y axis. This graph shows the relationship between the number of divisions to positivity and starting bacterial concentration. This allows starting bacterial concentration to be estimated using the values generated from the gompertz function.

Using the invention, any variation from the norm in a fluid can be detected, including a colour change due to either suspended colloidal particles or chemical reaction. A change away from transparency towards the red end of the spectrum will cause absorption of more red light, so changing the detection parameters. The same holds true towards the blue end of the spectrum but the detection parameters will be altered differently allowing differentiation and detection. Adding different coloured lasers boosts this capacity.

A skilled person will appreciate that variations of the disclosed arrangements are possible without departing from the invention. For example, although the main area of application described above relates to medical analytics, other applications are possible. For example, because the device can detect any particle in a non-opaque liquid, it could be used to find any particle in a liquid medium, such as dust, sand or grit in fluids such as high-quality bottled water. It could also be used to test fruit juices being imported, as they need to prove they are not carrying non-endemic bacteria or fungal spores. To do this, a threshold of scattering intensity can be used as a blank and any variation from this can be registered and recorded as a difference which has process significance. Accordingly, the above description of a specific embodiment is made by way of example only and not for the purposes of limitations. It will be clear to the skilled person that minor modifications may be made without significant changes to the operation described.

The invention claimed is:

1. A system for measuring at least one property of a liquid sample comprising biological material, the system comprising:

an integrating light collector comprising a cavity in which the liquid sample is at least partially contained, an entry port for allowing light to enter the cavity, an exit port to allow un-scattered light to pass to a beam dump, a first part comprising a sample port, and a second part separable from the first part and comprising a reflective surface that is configured to reflect light and thereby enable the integrating light collector to collect light scattered by interaction with the liquid sample;

a sample holder configured for containing the liquid sample comprising biological material within its internal volume and for at least partially containing the liquid sample in the integrating light collector, wherein the sample holder is inserted into the sample port such that the first part, the second part, and a portion of the sample holder form the cavity in which the liquid sample is at least partially contained;

a light source configured to introduce light in the integrating light collector such that the light is incident on the liquid sample at least partially contained in the cavity;

a signal generator or modulator configured to apply a known modulation of the light output by the light source;

a phase-sensitive detector comprising a lock-in amplifier, wherein the phase-sensitive detector is configured to detect scattered modulated light that is collected in the integrating light collector; and a processor configured to analyse the scattered modulated light detected by the phase-sensitive detector at a first time and the scattered modulated light detected by the phase-sensitive detector at a second time and determine a change in the detected modulated light as a function of time thereby to determine at least one property of the liquid sample selected from:

drug susceptibility of the biological material;

a change in a number of cells in the liquid sample;

a change in cell state; and a change in the biological material.

2. A system as claimed in claim 1, wherein the light source comprises a laser or LED.

3. A system as claimed in claim 1, wherein the light source has a wavelength in the range of 590 nm to 650 nm.

4. A system as claimed in claim 1, wherein the light source has a wavelength in the range of 620 nm to 750 nm.

5. A system as claimed in claim 1, wherein the known light modulation is at least one of a phase modulation, a frequency modulation.

6. A system as claimed in claim 1, wherein the sample holder is configured to hold a sample container containing at least part of the liquid sample substantially within the integrating light collector.

7. A system as claimed in claim 6, wherein the sample container comprises a sample cuvette.

8. A system as claimed in claim 1, wherein the phase-sensitive detector is provided on an internal surface of the integrating light collector and the system further comprises means for preventing un-scattered light from being detected by the phase-sensitive detector.

9. A system according to claim 1, wherein the processor is configured to analyze to determine at least the change in the biological material, wherein the change in the biological material is a change in a level or concentration of a pathogen in the biological material.

10. A system according to claim 1, wherein the biological material comprises at least one of: a species of strain of bacteria or fungi; a microbe.

11. A method for monitoring a biological material in a liquid sample, the method comprising:
    introducing the liquid sample into an integrating light collector thereby to at least partially contain the liquid sample;
    illuminating the liquid sample in the integrating light collector with light having a known modulation, so that the light passes through and is scattered by the liquid sample;
    detecting scattered modulated light collected in the integrating light collector, wherein the integrating light collector comprises a cavity in which the liquid sample is at least partially contained, an entry port for allowing light to enter the cavity, an exit port to allow un-scattered light to pass to a beam dump, a first part comprising a sample port, and a second part separable from the first part and comprising a reflective surface that is configured to reflect light and thereby enable the integrating light collector to collect light scattered by interaction with the liquid sample, and wherein the introducing the liquid sample into the integrating light collector includes inserting the sample holder into the sample port such that the first part, the second part, and a portion of the sample holder form the cavity in which the liquid sample is at least partially contained,
    wherein detecting scattered modulated light collected in the integrating light collector comprises detecting first scattered modulated light that is scattered in the integrating light collector at a first time and detecting second scattered modulated light that is scattered in the integrating light collector at a second time, and wherein the method further comprises:
    analysing the detected first scattered modulated light and the detected second scattered modulated light to determine a change in the detected modulated light as a function of time thereby to determine at least one of:
    drug susceptibility of the biological material;
    a change in a number of cells in the liquid sample
    a change in cell state; and
    a change in the biological material.

12. A method as claimed in claim 11, wherein the method comprises analyzing to determine at least the change in the biological material, wherein the change in the biological material is a change in a level or concentration of a pathogen in the biological material.

13. A method as claimed in claim 11, further comprising monitoring drug susceptibility by introducing a drug into the liquid sample and analysing to determine drug susceptibility.

14. A method as claimed in claim 11, wherein the liquid sample comprises at least one of a species or strain of bacteria/fungi; a microbe.

15. A device for measuring at least one property of a liquid sample comprising biological material, the system comprising:
    an integrating light collector comprising a cavity in which the liquid sample is at least partially contained, an entry port for allowing light to enter the cavity, an exit port to allow un-scattered light to pass to a beam dump, a first part comprising a sample port, and a second part separable from the first part and comprising a reflective surface that is configured to reflect light and thereby enable the integrating light collector to collect light scattered by interaction with the liquid sample;
    a sample holder configured for containing the liquid sample comprising biological material within its internal volume and for at least partially containing the liquid sample in the integrating light collector, wherein the sample holder is inserted into the sample port such that the first part, the second part, and a portion of the sample holder form the cavity in which the liquid sample is at least partially contained;
    a light source configured to introduce light in the integrating light collector such that the light is incident on the liquid sample at least partially contained in the cavity;
    a signal generator or modulator configured to apply a known modulation of the light output by the light source; and
    a phase-sensitive detector comprising a lock-in amplifier, wherein the phase-sensitive detector is configured to detect scattered modulated light that is collected in the integrating light collector, wherein detecting scattered modulated light collected in the integrating light collector comprises detecting first scattered modulated light that is scattered in the integrating light collector at a first time and detecting second scattered modulated light that is scattered in the integrating light collector at a second time.

16. A system as claimed in claim 1, wherein at least one of the first part and the second part includes a port for the light source and a port for the phase-sensitive detector.

* * * * *